(12) United States Patent
Schomburg et al.

(10) Patent No.: US 12,214,090 B2
(45) Date of Patent: Feb. 4, 2025

(54) KIND OF WOUND DRESSING FOR HAEMOSTASIS

(71) Applicant: SPEED CARE MINERAL GMBH, Neubrandenburg (DE)

(72) Inventors: Joachim Schomburg, Neubrandenburg (DE); Marta Loffler, Altentreptow (DE); Christian Schultz, Neubrandenburg (DE); Eckhard Salzsieder, Karlsburg (DE); Wolfgang Frohn, Schauenstein (DE)

(73) Assignee: SPEED CARE MINERAL GMBH, Neubrandenburg (DE)

( * ) Notice: Subject to any disclaimer, the term of this patent is extended or adjusted under 35 U.S.C. 154(b) by 751 days.

(21) Appl. No.: 16/631,184

(22) PCT Filed: Jul. 20, 2018

(86) PCT No.: PCT/EP2018/069761
§ 371 (c)(1),
(2) Date: Jan. 15, 2020

(87) PCT Pub. No.: WO2019/016367
PCT Pub. Date: Jan. 24, 2019

(65) Prior Publication Data
US 2020/0215220 A1 Jul. 9, 2020

(30) Foreign Application Priority Data
Jul. 21, 2017 (DE) .......................... 102017116511.8

(51) Int. Cl.
*A61L 15/18* (2006.01)
*A61L 15/40* (2006.01)
*A61L 15/44* (2006.01)

(52) U.S. Cl.
CPC ............... *A61L 15/18* (2013.01); *A61L 15/40* (2013.01); *A61L 15/44* (2013.01); *A61L 2300/102* (2013.01); *A61L 2300/404* (2013.01); *A61L 2300/418* (2013.01); *A61L 2400/04* (2013.01); *A61L 2400/12* (2013.01)

(58) Field of Classification Search
None
See application file for complete search history.

(56) References Cited

U.S. PATENT DOCUMENTS

2010/0036334 A1* 2/2010 Heagle ............... A61M 1/98
604/319
2016/0193380 A1 7/2016 Dubey et al.

FOREIGN PATENT DOCUMENTS

| CN | 101543565 A | 9/2009 | | |
| CN | 105561370 A | 5/2016 | | |
| CN | 106581729 A | 4/2017 | | |
| GB | 2221620 A | * 2/1990 | ............. | A61F 13/00 |
| WO | WO-2008118543 A2 | * 10/2008 | ............... | C08K 9/08 |
| WO | 2012001543 A2 | 1/2012 | | |
| WO | 2013191836 A1 | 12/2013 | | |

OTHER PUBLICATIONS

Soheilmoghaddam et al., Bionanocomposites of Regenerated Cellulose Reinforced with Halloysite Nanoclay and Graphene Nanoplatelets: Characterizations and Properties. In: Thakur, V., Thakur, M. (eds) Eco-friendly Polymer Nanocomposites. Advanced Structured Materials, vol. 75, Jun. 2015, pp. 295-321.*
Qi, C., Qian, X., The Application of Medical Fiber on Medical Textile, Proceedings of the 2010 International Conference on Information Technology and Scientific Management, available at chrome-extension://efaidnbmnnnibpcajpcglclefindmkaj/https://file.scirp.org/pdf/20-1.3.pdf, accessed on Oct. 4, 2023 (Year: 2010).*
94(3) Communication issued in corresponding EP Patent Appln. No. 18745555.5, dated Nov. 29, 2021.
Mehrosadat Alavi, et al., "The effect of a new impregnated gauze containing bentonite and halloysite minerals on blood coagulation and wound healing," Blood Coagulation and Fibrinolysis, Jan. 1, 2014, Seiten 856-859, XP055855698.
Int'l. Search Report for PCT/EP2018/069761, dated Nov. 6, 2018.
N.N. "IRW-News: I-Minerals Inc .: I-Minerals Halloysit-Produkt Ultra Hallopure wird vom deutschen Diabetes-Institut Gerhardt Katsch Karls burg in der Entwicklung von mineralimpragniertem Material zur Wundbehandlung verwendet" Jan. 18, 2017 (Jan. 18, 2017), Marketscreener, Retrieved from the Internet: https :/ /de.marketscreener.com/l-MINERALS-INC-21105 521/news/IRW-News-I-Minerals-Inc-I-Minerals-Halloy sit-Produkt-Ultra-Hallopure-wird-vom-deutschen-Dia betes-23 71096 7 / [retrieved on Oct. 18, 2018] XP002785843.
N.N. "Halloysite nanotubes incorporated into wound treatment cloth" Jan. 18, 2017 (Jan. 18, 2017), Nanotech, Retrieved from the Internet: http://www.nanotechmag.com/nanoclays-incorporated-wound-treatment-cloth/ [retrieved on Oct. 18, 2018] XP002785833.
Thomson Scientific, London, GB; , vol. 2017, No. 41, AN 2017-28530S, abstract No. 0, Retrieved from: Database WPI [online] XP002785847.
Alavi Mehrosadat et al. "The effect of a new impregnated gauze containing bentonite and halloysite minerals on blood coagulation and wound healing." Dec. 2014 (Dec. 2014), abstract No. Database accession No. NLM25004023, Retrieved from: MEDLINE [online] US National Library of Medicine (NLM), Bethesda, M D, US XP002785860 abstract.
Thomson Scientific, London, GB; , vol. 2016, No. 45, AN 2016-33627L, abstract No. 0, Retrieved from: Database WPI [online] XP002785865.
Thomson Scientific, London, GB; , vol. 2010, No. 23, AN 2009-P79280, abstract No. 0, Retrieved from: Database WPI [online] XP002785877.

* cited by examiner

*Primary Examiner* — H. Sarah Park
(74) *Attorney, Agent, or Firm* — MaxGoLaw PLLC

(57) ABSTRACT

A wound dressing is which has haemostatic, coagulation-promoting and biocidal properties and can therefore be utilized particularly for acute wound care. Typical areas of application for acute wound care are, for example, the treatment of gunshot wounds. The wound dressing features selected halloysites which, for example, are applied to textile fibers or non-woven materials.

17 Claims, 16 Drawing Sheets

| Properties | Halloysite |
|---|---|
| Hardness (Mohs) | 2.0 |
| Mineral density | 2.6 g/cm³ |
| Raw density | Ø 0.3 g/cm³ |
| Breaking index | 1.55 |
| Internal surface area | 20 – 60 m²/g |
| Morphology (tubes) | Normal > 90 % < 2μm<br>Length < 1 -2 μm<br>External Ø < 50 nm<br>Internal Ø < 10 – 20 nm |
| Aspect ratio | 5 – 30 |
| pH-Value | 5 - 7 |
| Colour | Grey – Ultra White (> 90 % Blue Filter) |
| Rawness | Very low (when crystalline silica oxide is present) |

Fig. 5

| Properties | Halloysite |
|---|---|
| Dioxin / Furan (naturally occurring) | Very low (< 0.5 ng/kg substitution degree {d.s.}) |
| Contains heavy metals (naturally occurring) | Total less than 100 – 300 ppm |
| Resistant against acids | High |
| Thermal stability | Up to 500 °C (Begin of loss of crystal water approx. 14 %) |
| Naturally occurring halloysite types | 10 Å – Halloysite<br>7 Å – Halloysite (dehydrated) |

| | |
|---|---|
| Foodstuff Classification | Yes (E 558) |
| IACR Classification | Yes (Class 3) |
| EPA Classification | Yes (Class 4A not toxic) |
| Pharmacopoeia (EU, US, UK) | Designated as (synthetic Bolus alba, Kaolinite {Engl.: China Clay}) |

Fig. 5A

| Criteria / Parameters | Variability in analysed halloysites from worldwide sources |
|---|---|
| Contained halloysite | 50 - 90 %, mostly mixtures of the 10 Å - and 7 Å - halloysite types |
| Contained silicate oxide | < 0.5 – 15 % (Quartz, Cristobalit)* |
| Contained alunite | Up to 20 % (only 3 instances are free of alunite) |
| Other contained minerals | e.g. Kaolinite up to maximum 60 %, feldspar, mica, smectites, sulphides, sulphates, ferrous minerals up to 10 % |
| Grain size distribution | 60 – 100 % less than 2 µm |
| Geometry of nanotubes | Length: 0.5 – 6 µm; external diameter: 60 – 120 µm |
| Aspect ratio | 5 - 30 |

* Crystalline silicate oxide is classified in Group 1 of IARC, more detailed information regarding contained > 0.1 % can be found in literature reference 1.

Fig. 5B

| HNT | Al$_2$O$_3$ | Fe$_2$O$_3$ | Morphology | | | | Aspect ratio |
|---|---|---|---|---|---|---|---|
| | | | | Ø diameter (nm) | | | |
| | | | Length | Internal- | External- | | |
| HNT 1 | 34.5 | 2.0 | 0.5 - 1.0 | 15 | 90 | | ~ 10 |
| HNT 2 | 25.0 | 23.0 | 0.3 - 1.0 | 25 | 120 | | ~ 8 |
| HNT 3 | 35.0 | 0.2 | 6.5 - 1.2 | 20 | 120 | | ~ 10 |
| HNT 4 | 37.5 | 0.4 | 0.6 - 1.2 | 20 | 100 | | ~ 10 |
| HNT 5 | 31.1 | 0.7 | 0.4 - 1.0 | 15 | 80 | | ~ 10 |
| HNT 6 | 35.5 | 0.3 | 0.5 - 1.5 | 25 | 90 | | ~ 12 |
| HNT 7 | 35.9 | 1.3 | 0.5 - 3.5 | 15 | 60 | | ~ 30 |
| HNT 8 | 36.0 | 0.8 | 0.3 - 1.0 | 20 | 100 | | ~ 10 |

Fig. 5C

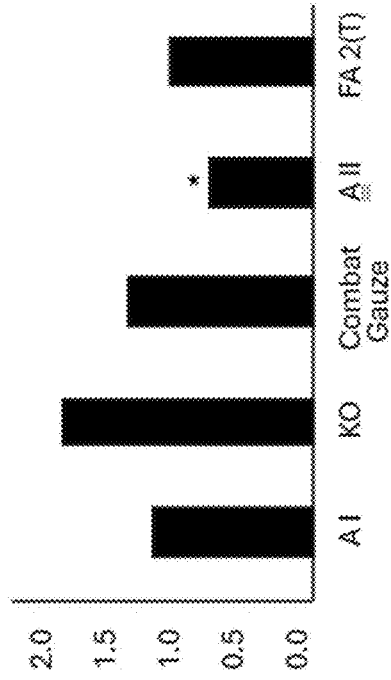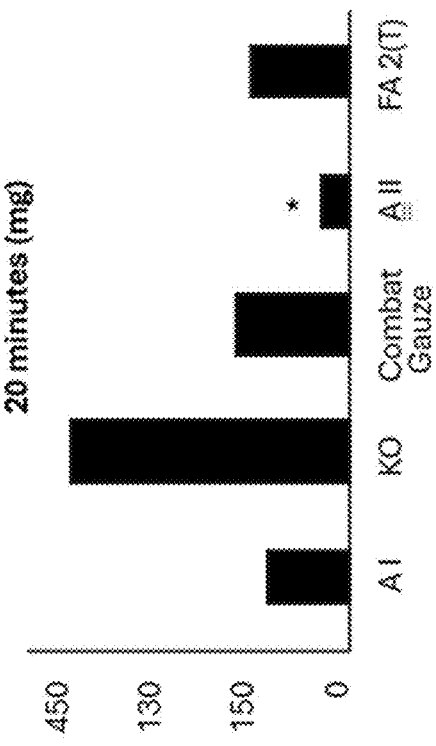
Fig. 13A
Fig. 13B

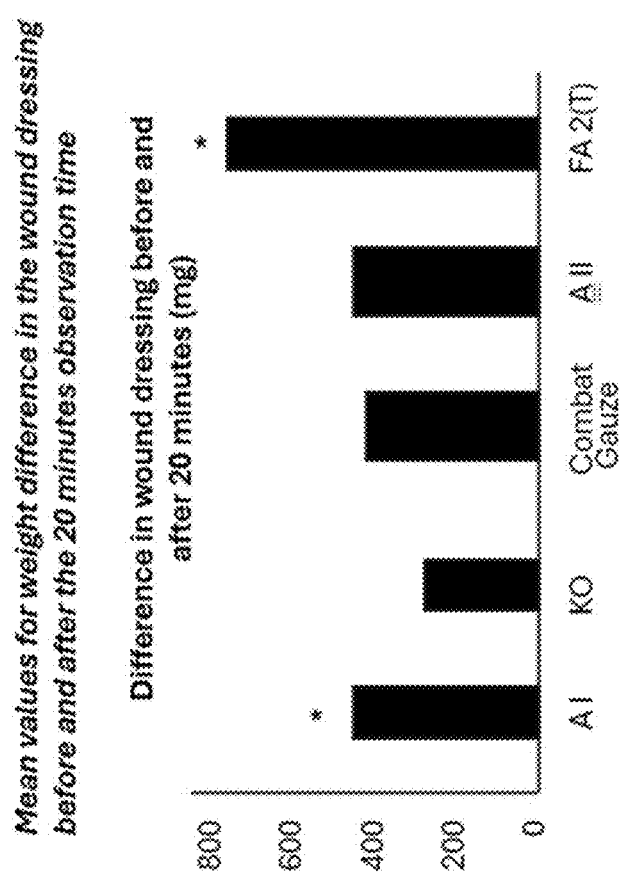

KIND OF WOUND DRESSING FOR HAEMOSTASIS

STATUS OF TECHNOLOGY

State of the art technology recognises several wound dressings for gunshot injuries. Many resources for treating gunshot injuries comprise, for example, bandages made of cotton or other types of materials. Furthermore, there are so-called gauze bandages which have a carrier-layer of gauze coated with chitosan. There are also known haemostatic bandages which are coated with kaolin, which thereby accelerate blood coagulation. In addition to kaolin, zeolite granules, three-layer silicates or diatomaceous earth can also be utilised for coating bandages. In the manufacture of mineral-based wound dressings, the mineral material application on the substrate is executed by technologies such as dipping or spraying, if necessary, using binders or chemical additives.

DISADVANTAGES IN THE STATUS OF TECHNOLOGY

The described state of the art indicates numerous disadvantages:
- High temperature developments (up to 70° C. with burns in the wound environment) and poor applicability in the case of zeolite granulates and other mineral granulates, as well as necessary wound cleansing after haemostasis;
- Inhomogeneities in the coating or impregnation of textile wound dressings due to the known technologies and poor detachability from treated wounds, as well as high manufacturing costs due to the use of various additives;
- Lack of purity requirements of the natural minerals utilised in the state of the art; the minerals do not fulfil the purity requirements of the pharmacopoeias and are therefore to be evaluated as critical with regard to medical product approval;
- With the currently known impregnation and coating technologies, only full-surface impregnation of the textile substrate can be achieved, which can thereby impede rapid throughflow;

OBJECT OF THE INVENTION

The object of the invention was to provide a wound dressing which did not indicate the disadvantages of the current state of the art. In particular, the object of the invention was to provide a wound dressing which combines the features of haemostasis with the features of reduced thrombosis risk. Furthermore, the object of the invention is to ensure that the wound dressing adheres very flexibly to the skin and is easily detachable from the wound after the acute wound care and therefore does not cause any new bleeding. The wound dressing should also be effective in the case of patients who are taking blood thinner medications or who have reduced blood coagulation activity independently of these medicines.

Solution for the Object

The above stated object is solved by a haemostatic wound dressing which is supported by a textile substrate, for example, made of composite fibres and halloysite. Textile substrates include, in particular, webbing, woven fabrics, knitted fabrics and/or non-woven materials. Accordingly, the invention relates to a novel mineral-impregnated textile wound dressing with surprisingly good haemostatic and biocidal effects combined with a reduced risk of thrombosis.

The invention-based wound dressing can be surprisingly applied as flexibly to the skin and is very easy to remove after acute wound care and therefore does not cause new bleeding. It is also surprising that, when using the wound dressing according to the invention, there is no temperature and/or germ load on the wound to be treated.

The halloysite can be distributed surprisingly well as homogeneously on the textile substrate, so that a good and fast blood absorption and flow through the textile substrate is guaranteed during the treatment of wounds.

It is to the inventors' credit that they have illustrated that the use of halloysites leads to surprisingly improved haemostasis, especially in the case of gunshot wounds, when the halloysites are applied to a textile substrate in the form of a wound dressing.

It was not obvious that these properties of improved haemostasis were associated with a surprisingly reduced risk of thrombosis.

Preferred Implementation Forms for the Invention

The preferred forms of implementation for the invention result from the subclaims.

In a preferred form, it is intended that the textile substrate on which the halloysite is applied should comprise composite fibres. It is also surprising that composite fibres are particularly well suited to absorb halloysites evenly or to be coated with halloysites. It was completely surprising that the combination of composite fibres and halloysites, and/or the combination created from composite fibres and halloysite coating, leads to a surprisingly good haemostatic and biocidal effect in wound care.

The layer of silicates of kaolinite and montmorillonite utilised to date are flaky and monopolar (negative layer charges), which therefore means that the effect on the shortening of the natural coagulation cascade is less in comparison with the tubular and bipolar halloysite according to the invention.

An additional advantage is that the very inventive wound dressing is perceived by the patient as much gentler than the state-of-the-art products. For this reason, the willingness to use the wound dressing for emergency care, for example, is much greater than is the case with currently known products.

Preferred composite fibres are, for example, materials made of viscose, milk protein fibres and/or algae.

Particularly preferred composite fibres are regenerated fibres such as e.g. Lyocell, Cupro, Viscose or Modal.

Regenerated fibres are preferred fibres which can be produced from naturally occurring renewable raw materials using chemical processes. These are particularly considered to be cellulose derivatives, for example from wood.

Synthetic man-made fibres or natural fibres can, of course, also be used preferentially. In the sense of the invention, synthetic man-made fibres are all artificial fibres which can, for example, be produced from natural or synthetic polymers as well as inorganic substances by utilising chemical-technical processes. For example, synthetic polymers such as polyester, polyamide, polyimide, aramid, polyacrylic and others can be utilised.

In addition, it is also possible to use fibres from natural polymers such as acetate, triacetate, alginate, protein fibres, chitin or elastodiene. Regenerated cellulose fibres are also preferred. The preferred viscose fibres are hereby considered to be those produced from cellulose by a viscose process.

The preferred modal fibres will be produced in a modified viscose process and therefore have a higher strength than dry or wet viscose. Lyocell is produced in a wet spinning process, whereby the fibres are characterised by a very high dry strength and wet strength. The preferred milk protein fibres may, in such cases, be linear macromolecules with at least 85% by mass of lactic acid ester units. Other preferred fibres are those which are created from cellulose fibres or protein fibres such as modified soya bean protein fibres, zein, casein fibres or artificial fibres produced by microorganisms.

It was completely surprising that composite fibres which comprise blends selected from the group of viscose, algae and/or milk protein fibres which have particularly beneficial properties in reducing haemostasis time periods. Furthermore, it was not especially obvious to the expert that these preferred composite fibres have a particularly good biocidal effect in combination with the halloysites and that they do not additionally indicate the disadvantages of the state of the art. These disadvantages hereby include, in particular, the unpleasant development of temperature and heat in the state-of-the-art wound dressings.

In an additionally particularly preferred design, halloysites in the form of halloysite nanotubes are applied, for example, to the above stated composite fibres or to other textile substrates. Surprisingly, the use of nanotubes results in particularly efficient, utilisable wound dressings. Utilising nanotubes leads to a wound dressing which enables haemostasis to be achieved particularly quickly and without subsequent or post-operative bleeding.

Halloysite-7 Å nanotubes and Halloysite-10 Å nanotubes are particularly preferred. Especially the preferred halloysite nanotubes are particularly surprisingly suitable for solving the problem according to the invention. This surprising effect also thereby occurs when not homogeneous nanotubes of the stated preferred nanotubes are utilised, rather mixtures of these. For example, it may be preferable to use a halloysite-nanotube mixture containing both Halloysite-7Ä and Halloysite-10 Å shares. It was not especially obvious to the expert that the preferred nanotubes had surprisingly good haemostatic effects without the disadvantages of the state of the art.

In a preferred implementation form of the invention, the halloysite nanotubes are intended to have the following dimensions: Internal diameter: 10 to 20 Nanometre, external diameter: 50 to 70 Nanometre and/or length: 0.3 to 4 Micrometre. It was completely surprising that halloysite nanotubes, with the particularly preferred dimensions, are particularly well suited to solve the problem according to the invention.

It is preferred when the halloysite and/or the halloysite material is treated at 200° Centigrade beforehand. It was surprising that the effect of the wound dressing could be additionally, and surprisingly, improved when the halloysite was pre-treated at a temperature of 200° Centigrade before being applied to the textile substrate or soaked with this.

The preferred method is therefore a treatment at 200° Centigrade with the Halloysite-10 Å share converted into a Halloysite-7 Å share. This conversion may essentially affect all Halloysite 10 Å shares or only part of them. An expert can, without being inventive, determine which proportion of Halloysite-10Ä shares is to be converted into Halloysite-7 Å share by reference to the duration of the treatment. A water plasma treatment may be implemented as preferred in advance to reduce the zeta potential of individual halloysite tubes and/or halloysite nanotubes and thereby improve their dispersion capacity.

It was completely surprising that new types of textile wound dressings could be therefore provided, which could be printed with halloysites or halloysite pastes from the preferred nanotubes using various printing technologies, in particular partial printing.

It can be preferable to adapt the utilised halloysite nanotubes to the purity requirements with regard to by-product proportions (e.g. crystalline silicate) and heavy metals by selection and processing methods. It was also completely surprising that the halloysite nanotubes stated above can be utilised as mineral components, as they possess the necessary degree of purity and are preferably applied to the textile fibres by means of printing technologies or directly incorporated into the textile substrates by means of various non-woven manufacturing processes, preferably with the spun lace process. For the printing process, a mineral water suspension with a small proportion of an acrylate, Tylose and/or gelatine binder is produced in a preferred version.

Screen printing technology enables an exact and varying impregnation of the textile fabric surface in contrast to known spraying and dipping technologies from the state of the art, so that the introduction of additional chemicals and agents, as provided for in the state of the art, can be dispensed off completely. The halloysite nanotubes are biocompatible and are not subject to the EU nanoparticle definition (>50%<100 nm) and are classified by the EPA as non-toxic/GRAS. The comprehensive classification and assignment of halloysites to their possible applications can be found in FIG. 5A.

The halloysites and/or halloysite-nanotubes can be applied to the tissue substrate in a preferred implementation form by means of a binding agent. Even if it seems initially obvious to utilise a binding resource to position and fix the halloysite on the textile substrate with a binder, it was surprising that the advantageous effect of the halloysite can be additionally improved by the binder.

The hereby invented textile fibres and wound dressings therefore represent innovative developments. They are based in particular on viscose/algae and/or viscose/milk protein fibre composites, which can also directly contain up to 30% halloysite nanotubes. Studies have clearly indicated the surprisingly good biocidal properties of such textile fibres, which is very advantageous with regard to a broad spectrum of wounds which have to be treated. Furthermore, studies have determined that a lower non-woven material density, than with state-of-the-art textiles (e.g. Z-Medica), shortens haemostasis times.

In a particularly preferred implementation form, the wound dressing is characterised by the fact that the following fibres have been used alternatively or as a mixture to produce the dressing:
  a) Lyocell fibres with up to 20% (volume %) algae supplement (preferably incorporated into the fibre)
  b) A mixture of viscose fibre and lactic acid fibre (preferably 50:50)
  c) A milk protein fibre containing up to 30% halloysite (preferably incorporated into the fibre)
  d) Milk protein fibres (100% preferred).

It is preferable that the halloysite content, which is incorporated in the fibre types, is dispersed into the spinning mass by a process within the framework of the fibre production and/or spinning-in process prior to extrusion and is thereby integrated into the matrix of fibres resulting from the spinning mass.

It is particularly preferred that the fibres are subsequently processed into non-woven fabric, woven fabric, gauze, knitted fabric, webbed fabrics or scrims in order to bind the textile substrate.

It is particularly preferred in this case that a paste produced from halloysite nanotubes, distilled water and, when using a medically safe binder based on a cellulose gelatine composition with a maximum volume fraction of 5%, is printed onto the substrate by means of a planographic printing process and is therefore fixed onto the substrate without the need for subsequent suction, washing away or shaking off of the material which is not fixed to the substrate surface.

It is particularly preferred that not the entire substrate surface is printed with the halloysite-containing paste, rather only an area proportion of 30 to 70% of the substrate.

In particular, the substrate loaded with halloysite preferably has a total weight of 25 to 145 g/m², preferably from 50 bis 80 g/m².

Sterilisation can be executed with gamma radiation or ethylene gas treatment after sorting and packaging.

Depending on the intended use, the wound dressings according to the invention may also contain, for example, synthetic and/or natural polymers such as polyacrylates, antibacterial substances such as iodine, silver, copper and zinc or mixtures thereof, natural rubbers, chitosans, alginates, hydrogels, hydrocolloids and/or polyurethanes. They may additionally contain oxidising inorganic and/or organic compounds, disinfecting chemical compounds, common filling agents and auxiliary materials, fragrances and/or colourants to enhance the disinfectant effect and/or, depending on the intended use. In accordance with the invention, the halloysite-based coatings which are described will be utilised for the production of wound healing materials, in particular compresses, plasters and/or dressings.

The preferred wound dressings, which can contain up to 30% halloysite nanotubes by mass and which are applied to viscose/algae and/or viscose/milk protein fibre composites, are surprisingly well suited for the initial treatment of gunshot wounds. Injuries with stabbing weapons can also be treated very efficiently. A volume of % preferably applies to the fibre compositions and a mass of % with the paste compositions.

The sorting and packaging of the described haemostatic wound dressing is surprisingly simple and can be implemented variably so that customised sorting and packaging can be represented for various applications such as emergency care, first aid or surgical patient care. In addition to the special and surprising haemostatic and biocidal effects of the innovative wound dressing, the surprisingly simple sorting and packaging is an additional advantage of this equipment. It is imperative in wound care that the dressings for the treatment of a wound can be sorted, packaged and provided according to the size of the wound involved. This is particularly important when the person concerned still has to move or when the wound area is subject to movement. Since the wound dressing must permit movement in these cases, it is therefore important that the wound dressing can be easily prepared as a wound treatment agent. Especially when utilised in the field or generally in crisis regions, it is important that tailor-made packaging is provided in a very short time.

Wound treatment resources within the sense of the invention can be halloysite textile substrates in the form of a wound dressing with a porous surface which is then placed on the wound. The dressing can be either a component of a plaster, a dressing material, a compress or even loose. The wound dressing may similarly be applied to, contained in, or incorporated into, compresses, plasters or bandages by other means or may be an integral part of a dressing material. This treatment may be executed on human beings or animals. Furthermore, emergency care kits for gunshot wounds, disposable nappies for bleeding patients, sanitary towels or nursing pads are preferred forms of implementation of the invention. In the sense of the invention, wound lactating materials can also therefore be, for example, pastes or porous or non-porous materials such as films, for example siloxane films, polyester films, polyurethane films. The material for utilisation in the treatment of gunshot wounds is preferably characterised in that the wound treatment agent is covered on the wound side by a porous textile fibrous material, in particular a non-woven, knitted or crocheted fabric and by a moisture-permeable film, which may also comprise antiseptic agents.

The wound dressing, according to the invention, can also be utilised as a general dressing resource. In the sense of the invention, one hereby refers to those materials from which a medical dressing can be produced. They are therefore also referred to as dressing material or colloquially as dressings. They are often stored as ready for use in the form of first aid kits. An additional distinction can also be made between sterile or at least low-germ wound dressings and non-sterile binding or luting material. Prepared ready-to-use, combined combinations of wound dressing and luting material are also preferred. Sterile wound dressings are compresses and dressing cloths. The luting material preferably includes gauze bandages, ideal bandages, elastic fixation bandages, tricot tubular bandages and triangular cloths.

Prepared ready-to-use dressings are preferably bandage packs and quick wound dressings.

In an additional preferred implementation form, the textile substrate is intended to indicate a density between 30 g/m² and 120 g/m², preferably 50 g/m². Surprisingly, the preferred density results in a particularly rapid coagulation and binding of the blood in the wound. It was completely surprising that the stated parameter ranges lead to the fact that the object according to the invention is solved particularly well.

In another preferred implementation form, it is planned that the composite fibres contain between 3% and 30% (volume %) algae and/or up to 100% milk protein and alternatively indicate a halloysite share of up to 30% in the fibres. The preferred share of composite fibres thereby results in a particularly good solution to the object in accordance with the invention. It is particularly advantageous that these preferred implementation forms can be very easily removed from the wound after acute treatment so that there is no post-operative or subsequent bleeding. An additional advantage of this preferred implementation form is that it can be utilised surprisingly effectively in patients who are taking blood thinners.

The invention therefore concerns, in one aspect, a haemostatic device (a haemostatic agent) comprising (a) a textile substrate comprising composite fibres of mixtures of viscose, algae and/or milk protein (b) a temperature-treated halloysite and/or (c) a binding agent for fixing the halloysite on the textile substrate. Utilising routine tests enables the expert to select and combine these components in such a way that, when coming into contact is made by this device with blood, then coagulation is prevented and bleeding of a wound is prevented in preferably less than 2 minutes.

In another preferred implementation form, the binding agent is intended to comprise 90% to 95% deionised water and 5% to 10% acrylate. This advantageously enables the treated halloysite material to bind particularly well to the substrate or to fix it to the substrate. It was surprising that no additional additives were needed for this purpose. The preferred wound dressing is particularly effective in stopping bleeding in surgery, during first aid, with emergency care or during treatment of chronic wounds. For the expert, it was not obvious that the wound dressing would result in a particularly good treatment for an acute or chronic wound according to the preferred implementation form.

In an additional preferred implementation form, the binding agent and/or halloy site material only covers part of the textile substrate surface or wound dressing. 30% to 70% of the substrate surface is preferably covered; binding agents and/or halloysite material are preferably applied to the substrate by means of a printing process (e.g. screen printing). It is preferred when the halloysites cover 30 to 70% of the surface of the textile substrate since, in this case, the germ load of the wound can be surprisingly reduced in not only acute but also in chronic wound care. It is important to reduce the germ load especially in the treatment of chronic wounds. The biocidal effect of the preferred wound dressing means that it can be utilised extremely efficiently both for the acute treatment of wounds as well as, for example, in the care of the elderly for the treatment of chronic wounds for rapid haemostasis and to prevent secondary bleeding.

In an additional preferred implementation form, the haemostatic device includes a proportion between 10 g/m$^2$ and 60 g/m$^2$ of the halloysite material, which has been preferentially exposed to rapid drying at 130° C. Surprisingly, this procedure results in a highly flexible and waterproof substrate. It is particularly important to be able to utilise a waterproof wound dressing for acute emergency care. State-of-the-art wound dressings can only be utilised with disadvantages in the event of accidents outdoors or in the event of gunshot wounds. Accidents often occur in connection with storms or floods. In these cases, state-of-the-art wound dressings often become soaked and thereby lose their effectiveness. They are then neither permanently suitable for haemostasis nor do they indicate any biocidal effect. Surprisingly, the preferred wound dressing can be utilised very well in both storm and crisis situations.

It is hereby preferable that the haemostatic device or wound dressing can be manufactured utilising treated halloysite material which is sterile and preferably in accordance with the pharmacopoeia criteria for kaolinum ponderosum/medical kaolin.

It is additionally preferred when the halloysite material has been treated at 200° C. to convert preferred Halloysite-10 Å shares completely into Halloysite-7 Å tubes. In addition, a water plasma treatment can be used beforehand to reduce the zeta potential of individual halloysite tubes and improve their dispersion ability. Halloysite material is utilised as preferred which contains less than 1% or substantially no inert mineral substances such as quartz, cristobalite, feldspar, alunite or mica, which often represent common contaminants or impurities. Surprisingly, the bleeding is also subsequently stopped or the blood is absorbed when the halloysite material is not too far from the wound, for example by a non-woven fabric or material which is positioned between the halloysite material and the wound. A particular advantage is that the wound is therefore not encrusted by the halloysite material, rather remains clean. Typical situations in which such a preferred wound treatment product is to be utilised are those in which an ordinary dressing material such as e.g. a plaster would be unfavourable or undesirable, for example for people or animals reacting allergically to the adhesive etc. It is also beneficial when bleeding must be stopped very quickly, or when the wound could be infected, for example in the case of bite injuries by animals or accidents in sport, or in the case of an injury caused by firearms or cutting and/or stabbing weapons Another preferred implementation form of the invention is to apply the halloysite to the textile substrate, for example as a halloysite paste or as another material provided, in particular by screen printing, letterpress printing, gravure printing or flat printing. Screen printing or flat printing process is the preferred method.

EXAMPLE—SPECIAL DESCRIPTION FOR THE INVENTION

In the following, the invention will be described in greater detail using examples and illustrations but without being limited to these.

Abbreviation Explanations

FIG. 1.: PES-V1: —Textile polyethersulfone, untreated
Textile polyethersulfone, only printed with acrylic binding agent
Textile polyethersulfone with binding agent and Halloysittype MF7 (60 gr/m$^2$), full surface coverage printing
PES-V2: —Textile polyethersulfone, untreated
Textile polyethersulfone, only printed with acrylic binding agent
Textile polyethersulfone with binding agent and Halloysittype MF7 (30 gr/m$^2$), full surface coverage printing
Cotton-nylon, untreated
Only printed with Tylose binding agent
Printed with Tylose binding agent and HNT MF7 after copper (CU) coating in NT plasma,
(biocide 30: 30 gr/m$^2$; biocide 60: 60 Gr/m2)$^2$) full surface coverage printing
Control: Natural coagulation time without wound dressing
FIG. 2.: Cotton with Tylose binding agent and different, natural HNT types MF2, MF4 (not-tempered) and MF4/200 (tempered at 200° C.), all 50 gr/m$^2$, full-service coverage printing Control: Natural coagulation time without wound dressing
FIG. 3. and FIG. 4.: —Cotton with Tylose binding agent and HNT MF7 (30 gr/m$^2$), with different printing patterns (F1-F3), whereby a variable ratio from printed and unprinted surface areas occurs (refer to photograph)
C. Gauze: Product from Z-Medica, U.S.A.
Control: Natural blood coagulation without wound dressing
FIG. 6.: —FA1: Textile aramide without binding agent and HNT MF7 paste printing (130 gr/m$^2$) full surface coverage printed
FA2: Textile aramide without binding agent and HNT MF7 paste printing (50 gr/m$^2$) full surface coverage printed
FV1a: —Non-woven fabric with acrylic binding agent and HNT MF7 (50 gr/m$^2$), 70% printed
FV1b: —Non-woven fabric with acrylic binding agent and HNT MF7 (30 gr/m$^2$), 60% printed
FV2: Non-woven fabric with algae supplement with HNT MF7 (30 gr/m$^2$) full surface coverage printed FV3 non-woven fabric mixture from viscose acid protein fibre and milk acid protein fibre with binding agent (5%)
    with HNT MF7 (30 gr/m$^2$), full surface coverage printed
Combat Gauze: Product from Z-Medica, U.S.A.
Control: Natural blood coagulation without wound dressing FIG. 7.: —FV1/5: Lyocell non-woven fabric with 5% binding agent and HNT MF7 (30 gr/m$^2$) full surface coverage printing
    FV1/10a: Lyocell non-woven fabric with 10% binding agent (Tylose) and HNT MF7 (30 gr/m$^2$) printed with pattern (approx. 70% of the surface area)
    FV1/10b: Lyocell non-woven fabric with 10% binding agent (acrylic) with HNT MF7 (30 gr/m$^2$) printed with pattern
(60% of the surface area)
    FA2/5a; Aramide with 5% acrylic binding agent with HNT MF7 (30 gr/m$^2$), 70% printed
    FA2/5b: —Aramide with 5% acrylic binding agent with HNT MF7 (50 gr/m$^2$), 60% printed
    FM1: Non-woven fabric with zinc oxide (16%) with 5% binding agent HNT MF7 (30 gr/m$^2$) full surface coverage printed (fcp)
    FM2: Non-woven fabric with zinc oxide (8%) with 5% binding agent HNT MF7 (30 gr/m$^2$) fcp
    FM4: Non-woven fabric (aramide 50%, viscose 42%, zinc oxide 8%) with 5% binding agent with HNT MF7 (30 gr/m)$^2$) fcp
    FMS: Non-woven fabric (viscose 96%, algae 4%) with 5% binding agent HNT MF7 (30 gr/m$^2$) fcp
    FM8: Aramide as knitted fabric with 5% binding agent HNT MF7 (30 gr/m$^2$) fcp
Combat G.: Product from Z-Medica, U.S.A.
FIG. 8./FIG. 9.: —Quikclot: Product from Z-Medica, U.S.A.
    f-speed: Lyocell with 5% binding agent with HNT MF7 (30 gr/m$^2$) with partial surface
area printing (approx. 60%)
    MF4: Lyocell with 5% binding agent with HNT MF4 (30 gr/m$^2$) with full surface area printing
    Control: Natural blood coagulation without wound dressing Abbreviation Explanation for Animal Experimental Trials (FIGS. 10-14)

KO: Control textile cotton without respective printing
AkCotton with 10% binding agent and HNT MF7 (30 gr/m$^2$) full surface coverage printing
AkCotton with 5% binding agent and HNT MF7 (30 gr/m$^2$) full surface coverage printing
FA2(T): Cotton with 10% binding agent with HNT MF7 (60 gr/m$^2$) Cu coated in NT plasma full surface coverage printed
Combat Gauze: Product from Z-Medica, U.S.A.
FIG. 1 illustrates the effect of textile underlays impregnated with halloysite nanotubes and binding agents on the coagulation time in the recalcified citrate plasma of a representative healthy blood donor compared to untreated starting materials containing only binding agents, as well as the additional cotton underlays impregnated with biocide 30 and/or biocide 60. Biocide 30 and Biocide 60 are details which refer to halloysite material coated with copper utilising NT plasma technology. This illustrates the surprisingly good effect of the textile underlays which are impregnated with halloysite nanotubes and binding agents on the coagulation time.

FIG. 2 shows the testing of new halloysite-based minerals for the coagulation time in recalcified citrate plasma from two representative healthy blood donors. Hallyosite-based minerals have a significant influence on coagulation or clotting time. Depending on the treatment of the halloysite-based minerals, this effect can be additionally improved in certain cases. The treatment from halloysite-based minerals can, for example, be a 200° Centigrade treatment. FIG. 3 illustrates the testing of new samples of mineral-impregnated textile underlays (FROHN) for coagulation time in recalcified citrate plasma on healthy blood donors (at 37° C.) in comparison to the uncoated base material and to state-of-the-art products (Combat Gauze). Compared to the uncoated base material, the mineral-impregnated textile underlays according to the invention illustrate a surprisingly improved effect on the coagulation time. Although according to the mineral-impregnated textile underlays of the invention, whereby they do not exhibit the many disadvantages of the state of the art, they still achieve the positive effects of particularly effective or particularly good competitor products of the state of the art without having their disadvantages. The advantageous results could be verified on the basis of various patients (refer to FIG. 4). Preferred properties of the minerals which were utilised to impregnate the textile underlays are illustrated in FIGS. 5 (A-C).

The following is an example of the manufacture of a preferred wound dressing. The object task here was to apply finely ground mineral halloysite to non-woven fabric in the manufacture of the preferred wound dressing.

Technology: Production of a print-capable, water-soluble paste. Application of the paste to the textile substrate in a screen-printing process. The applied paste is subsequently dried.
Screen printing
    Template specification
    Manufacturer's designation: Saatilene HI-R/PE AM 34.100
    PW
    Monofilament polyester fabric, linen weave
    Number of threads per cm: 34
    Thread diameter: 100μ
    Mesh width: 185μ
    Open surface area: 43%
    Fabric thickness: 173μ
    Theoretical colour volumes: 71 cm3/m2
    Specific cross section: 0.267 mm2/cm
    Type of printing: dot-Print
    Machine specification
    Manufacturer's designation: BUSER Hydromag F7 2100/20/08
    With gas operated dryer F 128.201 OG
    Technical plant specification:
    Maximum printing width cm: 1,700 mm
    Number of utilised printing factories: 1
    Screen printing system: Flat printing template
    Dryer temperature: approx. 120° C.
    Production speed: approx. 8 lm/minute
    Squeegee speed: approx. 1.2 m/s Paste recipe
  Master mixture
    Water: 900-950 gr
    Binding agent: 50-100 gr
    Follow-up products can be identified with the addition of a marker to the recipe.
    Total: 1000 g
    Stir halloysite carefully into the master mixture and prevent any lumps until the appropriate paste viscosity (63 dPas according to Haake VT02) has been achieved.
    Application quantity for halloysite as standard guideline value: approx. 250 to 300 g Examples of Haemostatic Effects of the Invention-Related Wound Dressing In Vitro Measurements of the Haemostatic Effect of Mineral-Impregnated Textile Wound Dressings 1 Experimental Methodology The blood donors for the in vitro tests were selected from healthy normal people and patients who, due to an increased risk of thrombosis from clinical indications, were being treated with thrombocyte aggregation inhibitor medication or vitamin K antagonists. The blood samples were taken by puncturing the vein in the crook of the arm using the Vacutainer System from Becton Dickinson (USA). The blood samples were stored in sodium citrate tubes and serum tubes, which were also obtained from Becton Dickinson. The plasma samples which were required for the tests were pipetted from the sodium citrate tubes after centrifugation and transferred to 50 ml centrifuge tubes. Both freshly obtained plasma samples as well as plasma samples were stored at −70° C. for up to 6 months in the test series.

To measure the influence of mineral-impregnated wound dressings, 1 cm² large pieces were cut from the test samples and transferred, together with 1 ml citrate plasma, into 12×75 mm test tubes of transparent plastic with a round base. After equilibration for 10 minutes at 37° C. in a water bath, coagulation was initiated by adding 500 ml of a freshly prepared 25 mmol/l $CaCl_2$ solution to initiate recalcifying for the plasma. The samples were mixed with plastic stirrers at short intervals during the subsequent incubation at 37° C. The coagulation time read out on the stopwatch was the time at which a clot with graft formation was clearly recognisable in the corresponding test tubes. Since the coagulation in the mixtures with the different test patterns sometimes started at short intervals, not more than 3 test tubes were processed by each examiner simultaneously.

1 ml aliquot was immediately transferred to the test tubes with the test sample of mineral-impregnated wound dressings after blood collection for the measurement due to coagulation starting immediately in the serum tubes. The additional handling of the test mixtures with the whole blood samples and the determination of the coagulation time was executed in the same way as in the test mixtures with recalcified citrate plasma as described above. In preliminary tests for determining the most effective minerals, these were tested under the same conditions before textile impregnation in powder or granulate form and then added to the plasma and whole blood samples in a concentration of 100 mg per millilitre.

2 Implemented Materials

As mentioned in the section for experimental methodology, the Vacutainer System from Becton Dickinson with 7 ml sodium citrate and serum tubes from the same manufacturer were utilised for the blood samples.

The following minerals were implemented in powder form or granular form: MF2, MF4, MF4/200, MF7, Quik-Clot, f-speed and Kaolinit.

The utilised textile samples, with and without mineral impregnation, comprised: PES-VI, PES-V1-MF7, PES-V2, PES-V2-MF7, Cotton, Cotton-MF7, Vokano, 1764 Natural, 1764 White, 5150 Petra, 1611/014, 1144, 1267/400, 1267/500 (cotton fabric with different fabric densities and fibre thicknesses), AI, AII, AIII, AIV, BI, BII, BIII, BIV, FR1, FR2, FR3, FR4, FA1, FA2, FV1a, FV1b, FV2, FV3, FV1/5, FV1/10a, FV1/10b, FA2/5a, FA2/5b, FM1, FM2, FM4, FM5, FM8 and Combat Gauze.

3 Representation of Results and Findings Evaluation

The best acting powder minerals and textile underlay were determined with regard to reducing the coagulation time in recalcified citrate plasma and in whole blood in the first examination series using the described in vitro test systems. The mineral-impregnated FA2, FV3 and FM5 wound dressings emerged as the best examples from the combination of these results and their utilisation in additional development work as they performed as the best with regard to the reduction of the coagulation time, the textile dressing utilised and the stability of the mineral impregnation (FIGS. 6 and 7). FIG. 6 shows: In vitro testing for the influence of mineral-impregnated cotton underlays from the FA and FV series on the coagulation time in the recalcified citrate plasma of a representative healthy blood donor in comparison to the competing product of Combat Gauze.

FIG. 7 shows: In vitro testing for the effect of mineral-impregnated cotton underlays from the FV1, FA2 and FM series on the coagulation time in the recalcified citrate plasma of a representative healthy blood donor in comparison to the competing product of Combat Gauze.

The optimised mineral-impregnated FA2, FV3 and FM5 cotton samples enabled the coagulation time in vitro in both recalcified citrate plasma and whole blood from healthy blood donors to be reduced from 6 to 8 to slightly less than 2 minutes. In comparison to the Combat Gauze USA product, the wound dressings preferred according to the invention reduce the coagulation time in the same way or slightly more depending on the blood donor. During the in vitro tests executed in clear recalcified citrate plasma, it became apparent that the Combat Gauze competitor product results in a significant clouding of the plasma within a few seconds due to mineral detached from the textile base. In the practical application of Combat Gauze, it can therefore be assumed that detached mineral is rinsed out of the wound area and the haemostatic effect of the competitor's product thereby diminishes. Such type of clouding of the plasma was not observed in the wound dressings preferred according to the invention i.e. the own wound dressings are characterised by a higher stability of the mineral impregnation compared to the competing product.

The outstanding importance gained here is the evidence provided by the established in vitro test system that the coagulation time in whole blood and citrate plasma of thrombosis risk patients can be reduced to 2 minutes by treatment with anticoagulants with the wound dressings preferred according to the invention as with the healthy controls. In the absence of the mineral-impregnated wound dressings, the coagulation time in the control approaches was extended to 20 minutes in these patients by introduction of thrombocyte aggregation inhibitor and vitamin K antagonists compared to 6 to 8 minutes with healthy blood donors. This therefore means that in patients at risk of thrombosis with an increased tendency to bleed, taking so-called "blood thinners" with the developed optimised haemostatic wound dressings enabled a 90% reduction in the coagulation time to be achieved.

SUMMARY

Figure 1:
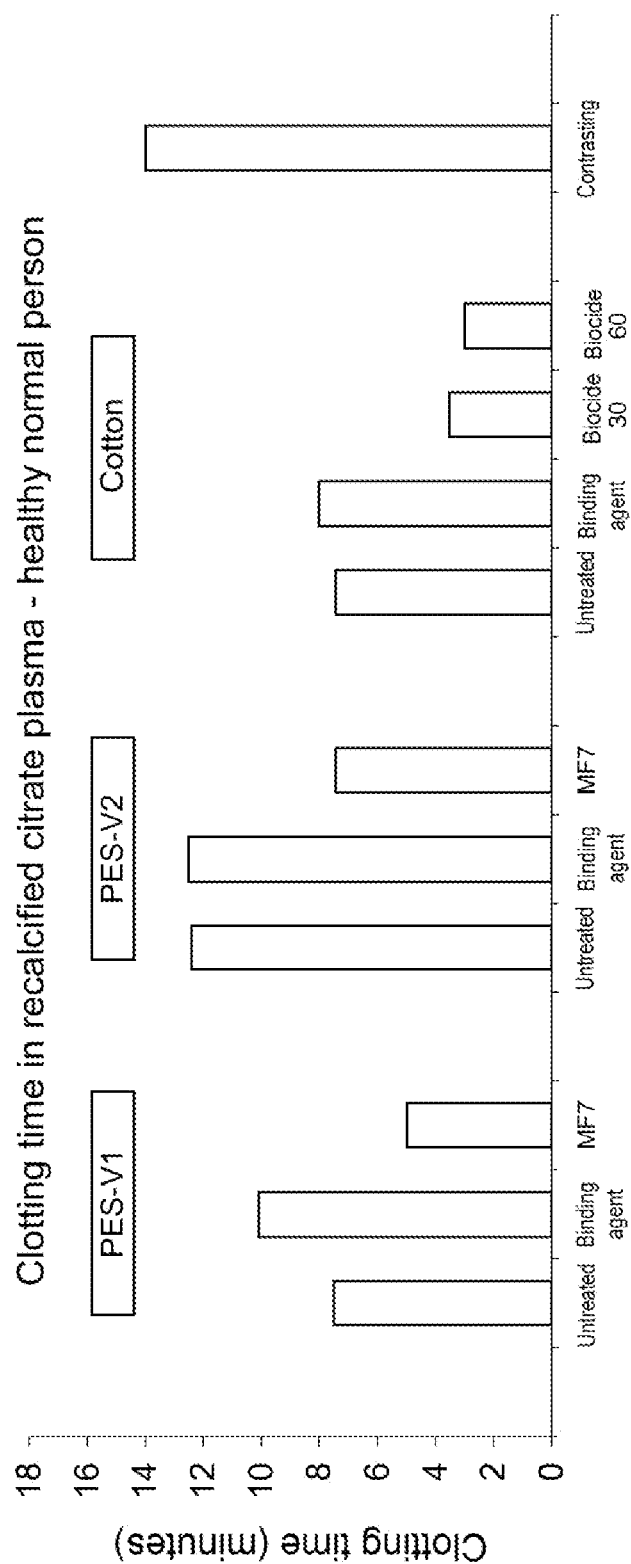
Figure 2:
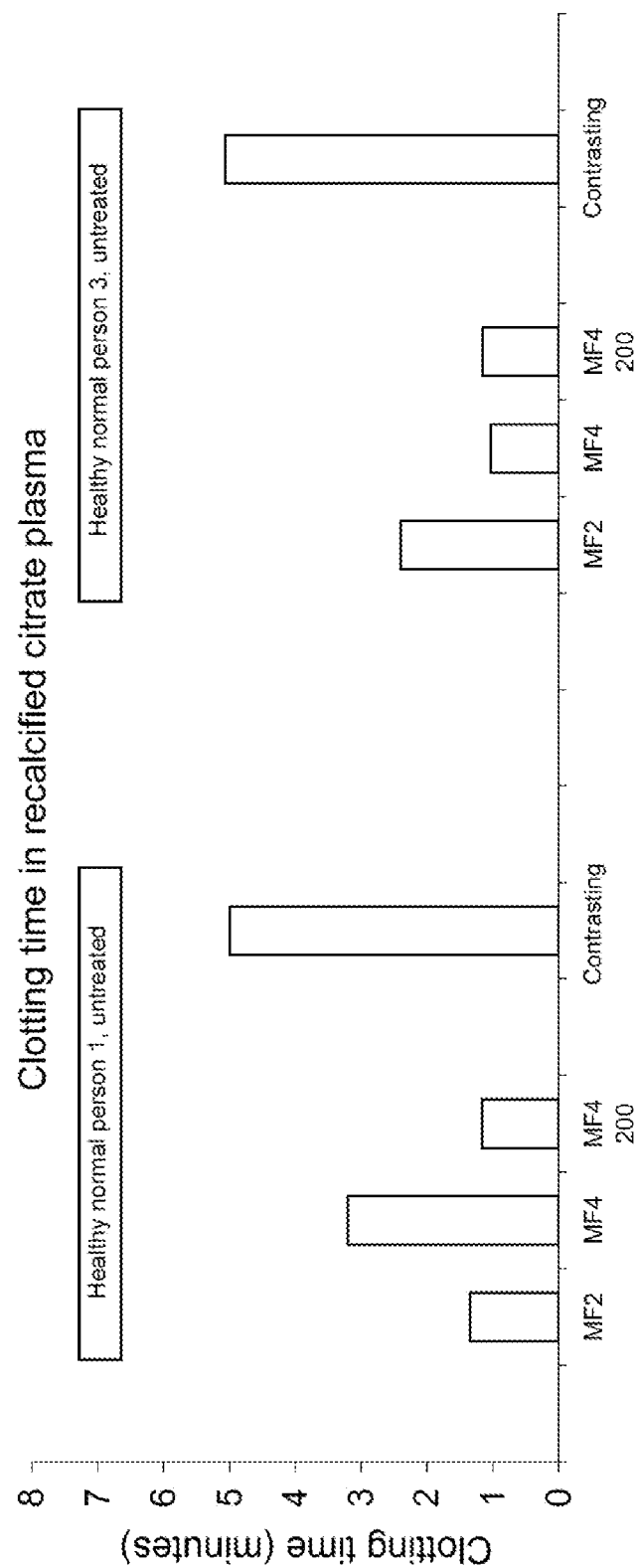
Figure 3:
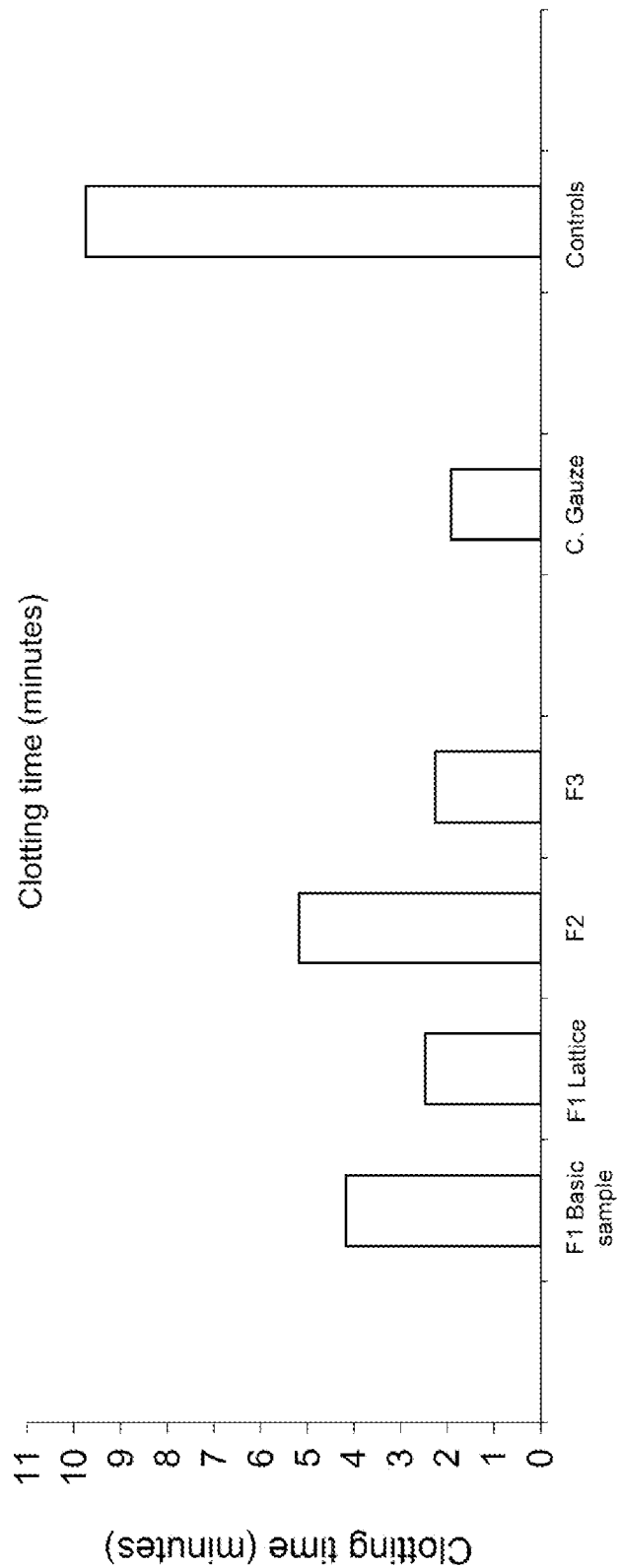

The mineral-impregnated wound dressings according to the invention such as FA2, FV3 and FM5 are equivalent to the Combat Gauze competitor product in their haemostatic effect, but are also characterised by a higher stability of the mineral impregnation.

The wound dressings according to the invention are also able to completely overcome the pharmacological coagulation inhibition induced by vitamin K antagonists and thrombocyte aggregation inhibitors and the associated bleeding tendency and thereby reduce the coagulation time in thrombosis risk patients treated with these medications to 2 minutes as with healthy blood donors.

Processes for Printing and/or Impregnating the Textile Substrate

The textile substrate utilised is a non-woven fabric, which is produced in the spun lace process or alternatively a needle-type non-woven fabric.

The fibres are bonded by water jetting at high pressure in the spun lace process and the fibres are bonded by needles in the needle-type non-woven fabric.

Utilising an embossing roller enables a surface with a perforated structure to be created on the non-woven fabrics, which makes it easier to detach the wound dressing from the wound which is being treated.

Furthermore, halloysite powder can already be dispersed into the milk protein spinning mass during the fibre spinning process so that the resulting spun thread can contain up to 30% halloysite. The non-woven fabrics utilised can be loaded differently and can contain fibres that can be combined.

The textile substrate may contain Lyocell or other cellulose manufactured fibres or from manufactured milk protein fibres and/or mixtures of the aforementioned, as well as admixtures of halloysite and/or algae which are already embedded in the fibres during the fibre spinning process.

For printing by means of a screen-printing process, a printable paste is produced from halloysite powder (250-300 g), water (950 g) and binding agent (50 g) and then applied to the textile substrate via a planographic printing template at a squeegee blade speed of 1.2 m/s and subsequently dried at approx. 120° C. Cellulose-gelatine mixtures or copolymers based on styrene and acrylic acid esters are utilised as water-soluble binding agents. The paste viscosity is 60 dPas according to Haake.

The sorting and packaging of the printed textile substrates is executed by means of a push knife cutter, laser cutter or ultrasonic cutter in order to obtain precise cutting edges. Sterilisation and packaging is subsequently executed.

Another exemplary manufacturing process for the wound dressing is executed out according to the following steps:
1. Active Mineral: Natural Halloysite Nanotubes (HNT's)
    By utilising appropriate temperature introduced into the treatment in the 7 A-form and additionally in the low temperature plasma with biocidal properties equipped for the used natural halloysite, the verification for the fulfillment of the purity requirements for Kaolinum Ponderosum/Medical Kaolin was implemented. The halloysite nanotubes are biocompatible and are not therefore subjected to the EU nanoparticle definition (>50%<100 mm) and are classified by the EPA as non-toxic/GRAS (4a).
2. Utilised Textile Threads and Non-Woven Fabric
    The following fibres are also preferably used as a mixture:
    a) Lyocell fibres with up to 20% (volume %) algae supplement (incorporated into the fibre)
    b) A mixture of viscose fibre and lactic acid fibre (50:50)
    a) Lactic acid fibres with up to 30% halloysite share (incorporated into the fibre)
    h) Non-woven fabric produced from 100% lactic acid fibres.
    The halloysites are dispersed by means of a process during the manufacturing for the fibres/spinning mass and are thereby integrated into the matrix of the fibres resulting from the spinning mass.
    In order to be able to form the textile substrate, the fibres are subsequently processed into non-woven fabrics, woven fabrics, gauze, knitted fabrics, crotched fabrics or scrims according to the exemplary and other possible preferred manufacturing processes.
3. Impregnation Technology
    A printing process (screen printing, flat printing) is preferred for applying a paste onto the textile underlay which contains HNT. This therefore provides the possibility to control the ratio of impregnated to non-impregnated textile surface in wide surface areas, which is important with regard to blood absorption and adhesion to the wound which is to be treated.
    Halloysite paste production is preferably executed by dispersing halloysite powder into distilled water with the addition of 1-5% water-soluble binding agents (based on a cellulose-gelatine composition). After printing has been completed, subsequent suction, washing off or shaking off of the excess mineral product can be omitted.

The application for wound treatment is preferably executed by the direct application of mineral granules or in combination with textile gauze fabric or non-woven fabrics, which are holistically coated with mineral particles and other additives by various technologies (dipping, spraying) (US 2016 0193380 A1, U.S. Pat. No. 907,878 B2).

The essential disadvantages of mineral-based wound dressings manufactured according to the state of the art are:
   High temperature development during application (up to 70° C., which will result in burns in the wound environment) and poor applicability/dosage in the case of zeolite granules and other mineral granules.
   Inhomogeneities in the coating or impregnation of textile wound dressings due to the previously utilised technologies and weaved materials (up to 10 pm large mineral particles) and, currently, and poor detachability from treated wounds, as well as high manufacturing costs due to the share of various additives,
   The verification for the purity requirements (sulphur contents; contaminants, lead, arsenic, cadmium, mercury and contents of other crystalline mixtures) for the natural minerals utilised so far (e.g. kaolinite, montmorillonite) for which various Parmacopes are specified for products located on the market has not been provided to date.

The preferred wound dressings do not have these disadvantages.

The variability of the density of the textile substrate (30-120 g/cm$^2$) and the fibre-incorporated and/or printed halloysite nanotube quantity (3-60 g/cm$^2$) enables very flexible sorting and packaging for the textile wound dressings, so that a tailor-made variance can be achieved for a wide range of applications such as emergency care, first aid or surgical hospital care.

Animal Experiments on Acute Haemostasis with Heavily Bleeding Wounds

1 Setting Objective

The principle implemented for the in situ/vivo study was to test the coagulation-promoting and/or accelerating effects of halloysite-coated tissue pieces (i.e. preferred designs of the wound dressing according to the invention) which had previously been successfully tested in in vitro experiments. The potential coagulating wound dressings should be tested on an organ which is bleeding profusely as (in situ).

2 Material and Methods 2.1 Study Design

Anaesthetised Wistar rats were provided with a catheter for arterial blood pressure measurement to be able to record blood pressure continuously. Fluid and anaesthetic post-dosing were administered via a venous catheter during the experiment. A blood sample was taken after completed instrumentation and subsequent equilibration (20-30 minutes).

The abdominal cavity was opened along the linea alba under deep anaesthesia with aspiration. A catheter was inserted into the bladder to prevent urinary retention during surgery. The left kidney was made visible and accessible by covering it with a non-absorbent sterile surgical drape and pushing the intestinal convolute to the side. The caudal renal pole was carefully detached from the surrounding fatty tissue. An approx. 2-3 mm thick piece of the caudal renal pole was now removed. Massive bleeding was then induced from this "0 minute" time point. Immediately after removal of the kidney pile, the wound dressing which was to be tested was placed directly on the wound.

During the following observation period of 20 minutes, the blood pressure was recorded and a volume substitution with physiological saline solution+1% BSA (bovine serum albumin) was subsequently implemented. The liquid and coagulated blood in the abdominal cavity was collected and measured at the end of the observation period and the blood on the wound dressing was examined.

The mean arterial blood pressure was recorded during the entire observation period. Mean values for respectively 1 minute were formed within the first 10 minutes after wound settlement for the evaluation, followed by the mean value for the period 10-20 minutes after wound settlement.

2.2 Test Groups

| Group | Quantity | Treatment |
|---|---|---|
| Test Group 1 = AI | 8 | Wound Dressing A I |
| Controls | 8 | Wound dressing uncoated, basic material for AI and AII |
| Reference Group = Combat Gauze | 8 | Wound dressing, Combat Gauze (Cobat Medical Systems) |
| Test Group 2 = AII | 8 | Wound Dressing AII |
| Test Group 3 = FA2(T) | 8 | Wound Dressing FA2(T) |

2.3 Parameters

For describing blood loss: Hematocrit (HK) before and 20 minutes after wound settlement
  Amount of blood and coagulation after 20 minutes in the abdominal space
  Blood pressure procedure, maximum
  Blood pressure drop, time up to achieving the blood pressure initial level again
  Weight of the wound dressing before and after (+20 minutes) of the application For describing wound dressing: Description of the condition before the removal
  Description of the behaviour before the removal
  Observation of post-bleeding after removal 3 Results 3.1 Blood Loss 3.1.1 Reproducibility of Wound Size In order to be able to estimate the reproducibility of the wound size in the selected model, the weight of the removed kidney pole was determined and the mean values contained in Table 1 were thereby obtained for the groups.

TABLE 1

Weight of the removed kidney piece (mean value ± SD)

| | AI | KO | Combat Gauze | AII | FA 2(T) |
|---|---|---|---|---|---|
| Weight of the kidney pole [mg] | 109 ± 36 | 122 ± 44 | 140 ± 30 | 115 ± 30 | 128 ± 19 |

3.1.2 Blood Pressure

Figure 10:
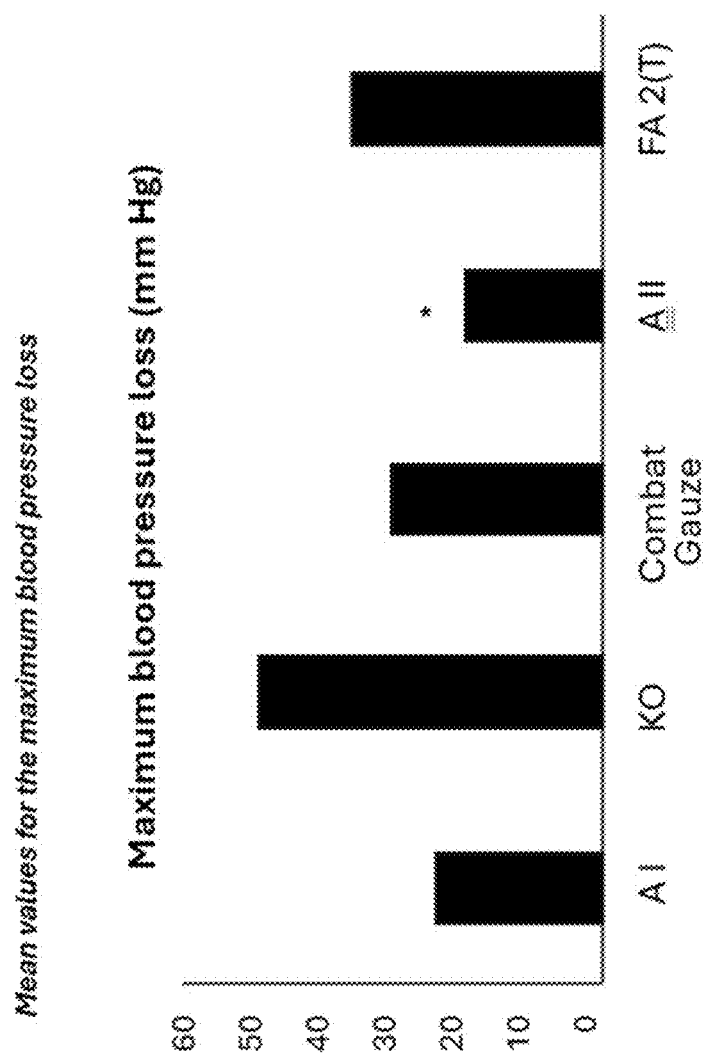

The highest blood pressure drop of 50±25 mmHg was measured in the control group (FIG. 10). Not only the reference material (Combat Gauze) but also the test materials resulted in a blood pressure drop reduced by up to half. The lowest drop could be observed after applying A II (FIG. 10). The lowest blood pressure was measured as a mean after 2-3 minutes.

Figure 11:
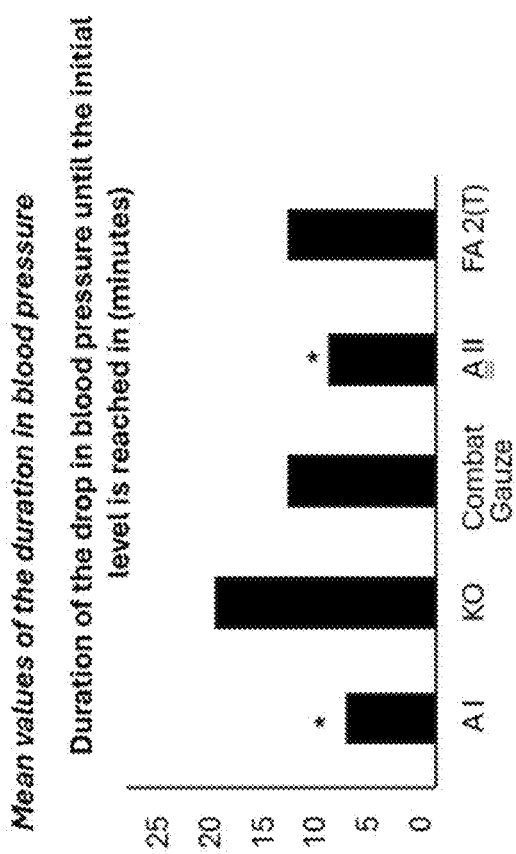
Figure 12:
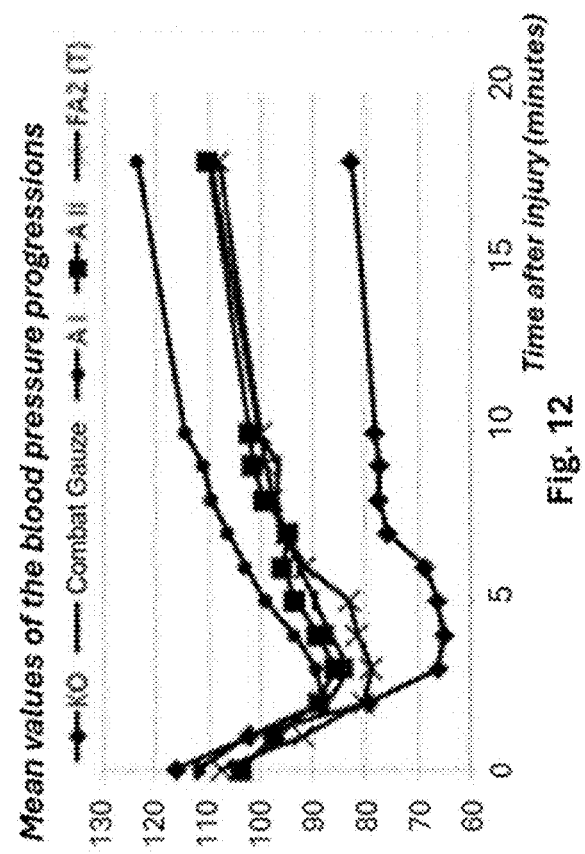

While the initial level in the control group was only initially reached on average after 18.8±4.1 minutes and partly not again in the individual animal, the blood pressure in A I already rose on average after 7.5±2.1 minutes and in A II after 9.1±7.3 minutes to the initial value again (FIG. 11, FIG. 12).

3.1.3 Haematocrit

Blood loss in the control group results in a decrease in haematocrit to 89% of the initial value. The loss of the haematocrit during the observation period of 20 minutes is slightly (91% of the initial value) in the reference group (Combat Gauze), in A I (93%) and in A II (94%) and significantly lower in FA2(T) (95%).

3.1.4 Quantity of Blood in the Abdominal Cavity

The largest amount of blood and the largest coagulation had accumulated in the control group at the end of the observation period. The measured amounts in the reference object, and especially in the test groups, indicated a lower bleeding rate. The effect was most pronounced after the application of AII (FIG. 13).

3.1.5 Suction Capability of the Wound Dressing

Figure 4:
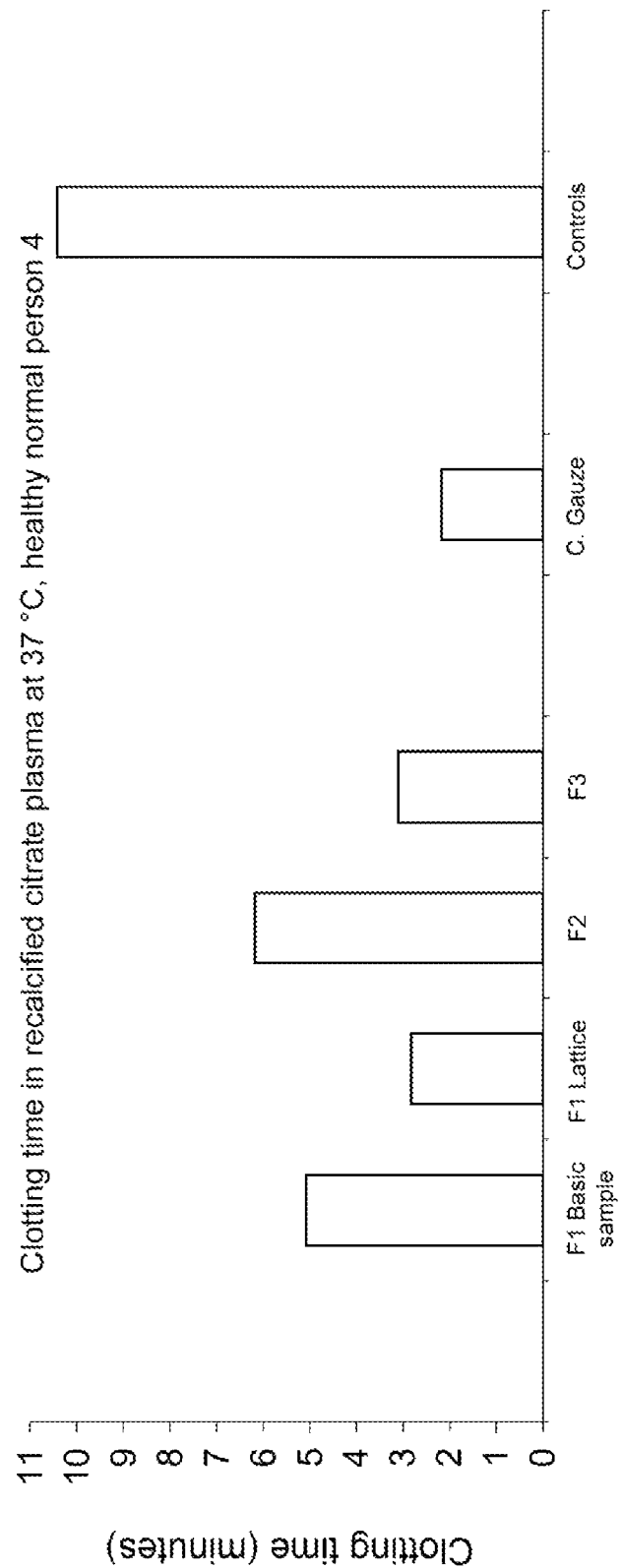
Figure 6:
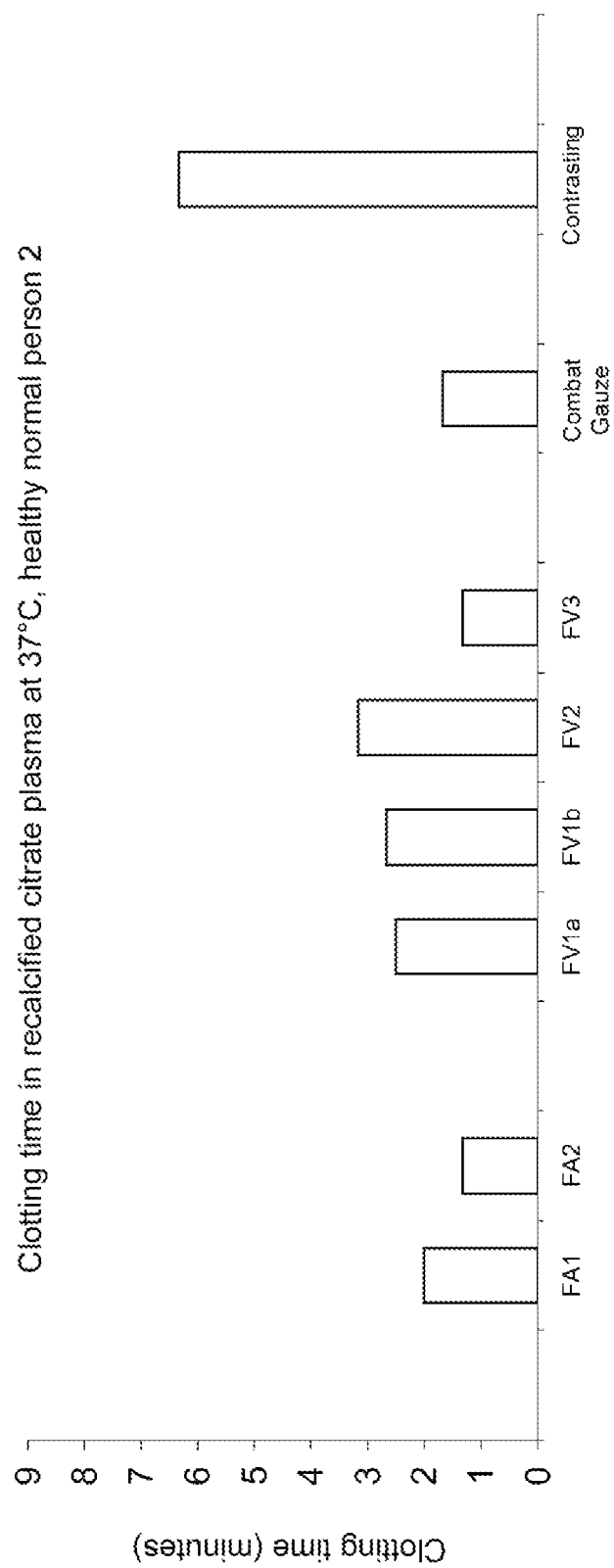
Figure 7:
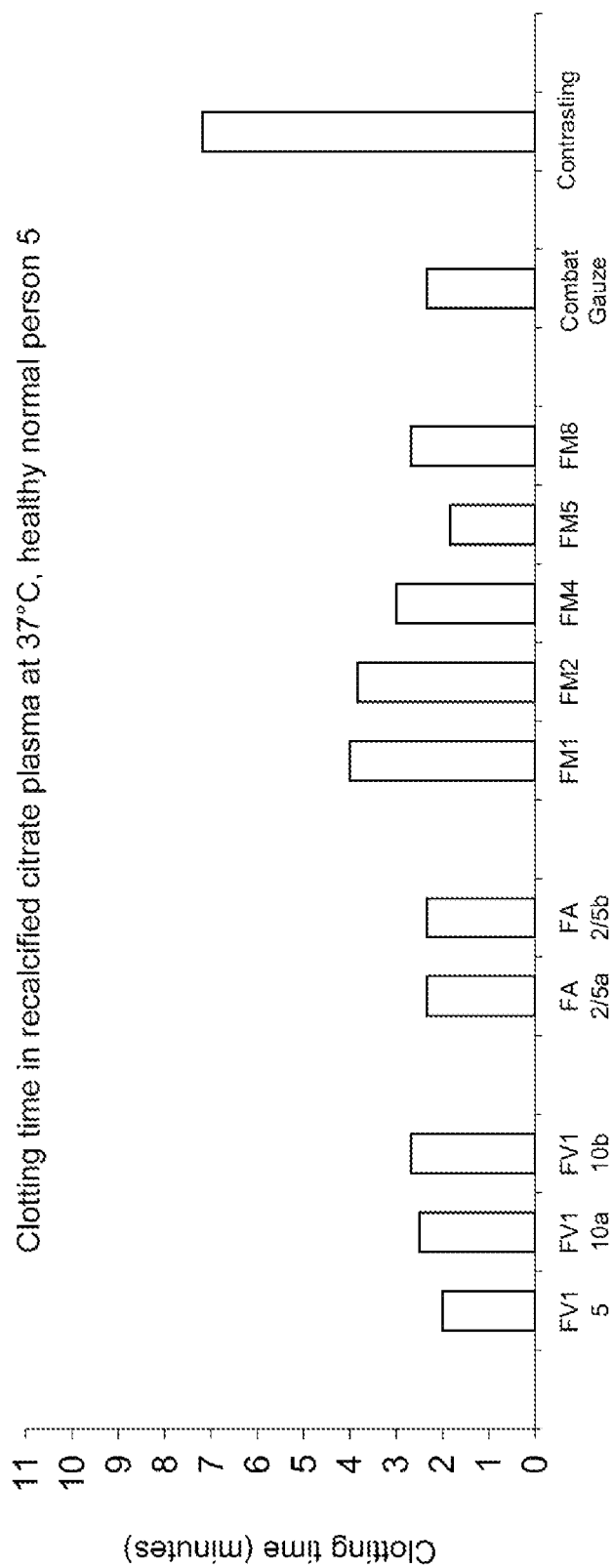
Figure 8:
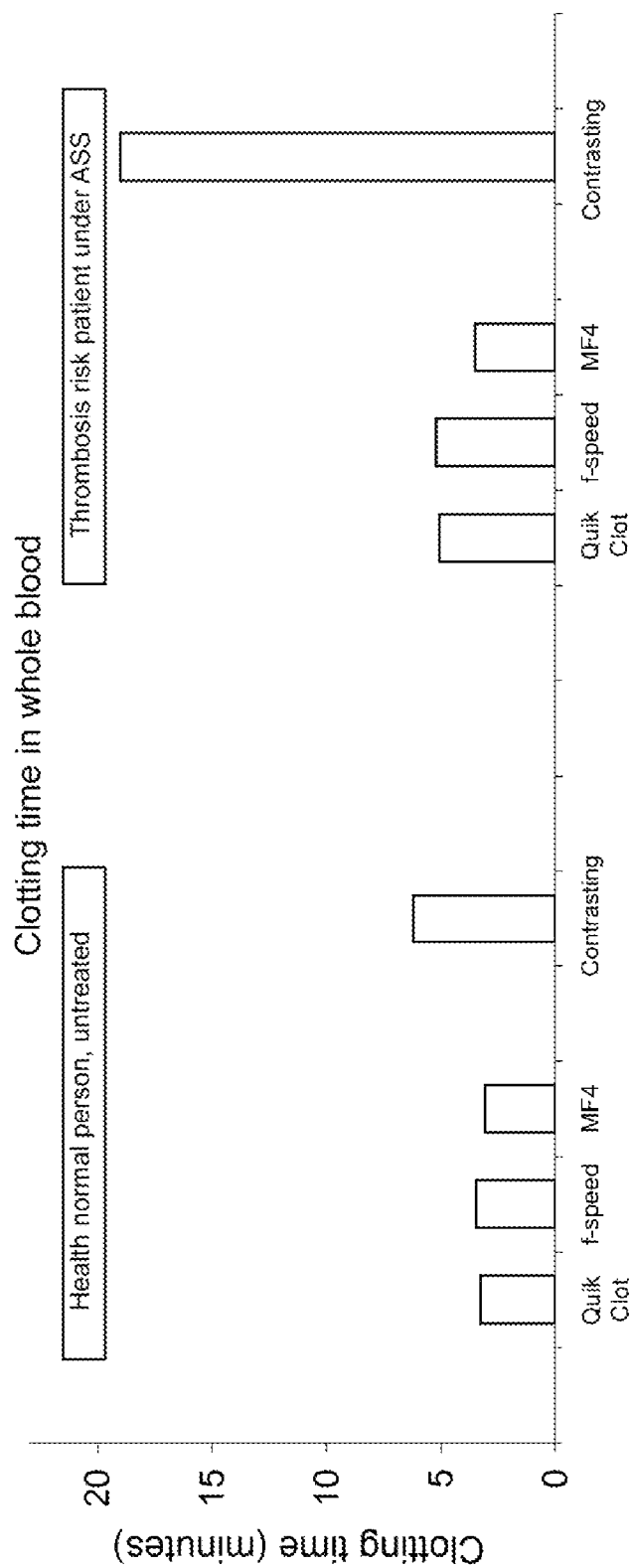
FIG. 8 shows: Effects of haemostatic powder minerals on the coagulation time in whole blood of a healthy blood donor compared to a representative thrombosis risk of a patient treated with the ASS thrombocyte aggregation inhibitor.
Figure 9:
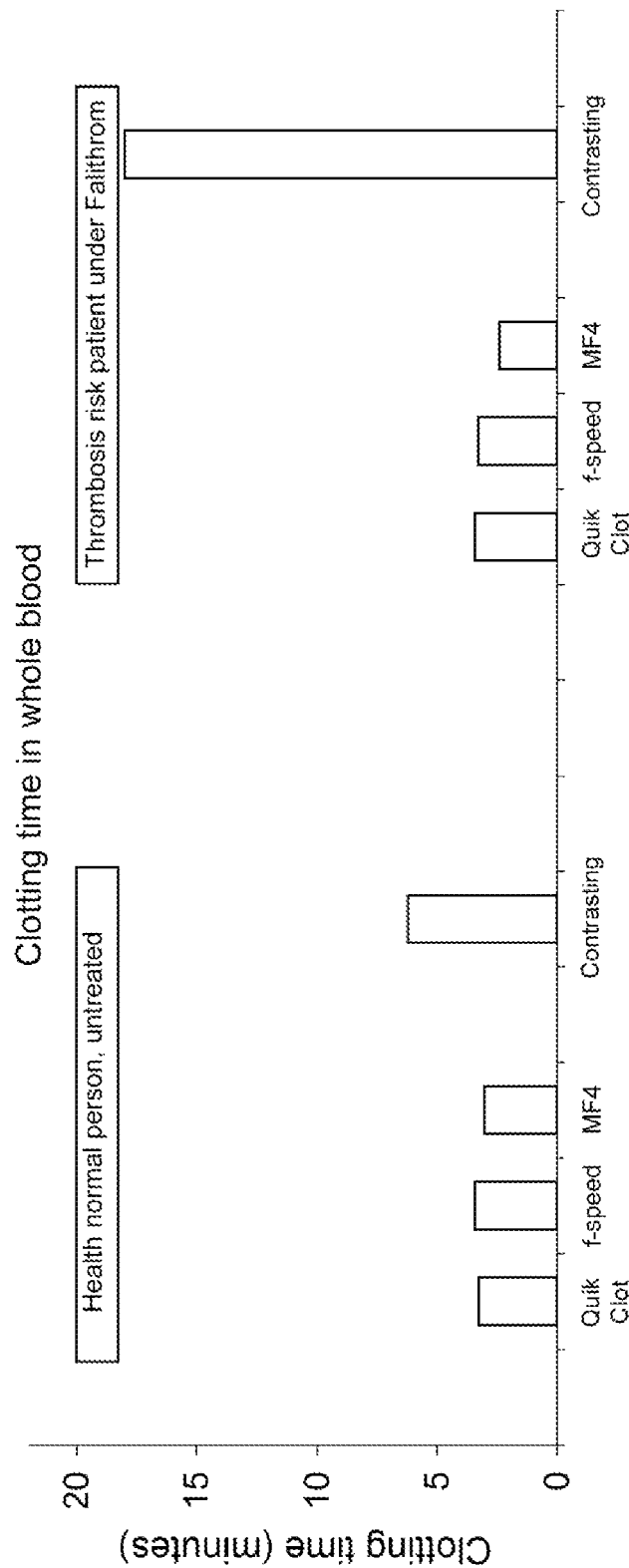
FIG. 9 shows: Effects of haemostatic powder minerals on the coagulation time in whole blood of a healthy blood donor compared to a representative risk of a thrombosis patient treated with the vitamin K Falithrom antagonist.

The formation of the difference between final weight and initial weight indicated that the control material was less absorbent, Combat Gauze, AI and A II bound more blood and FA2(T) was obviously most absorbent and/or promoted more coagulant (FIG. 4, FIG. 13).

3.2 Observing the Wound Dressing

The wound dressing in the control group optically appears somewhat stiff and firm and not very absorbent. The wound dressing lies almost loosely on the kidney pole after an observation period of 20 minutes. The Combat Gauze reference material is very thin, collapses very easily on contact with blood, adheres to the wound and can be loosened easily after 20 minutes, whereby a slight post-operative or subsequent bleeding is thereby induced. The A 1 and A II test materials adhere to the kidney, but can be easily loosened after the observation period and cause minor post-operative or subsequent bleeding. The FA 2(T) test material (refer to above) adheres easily to the wound and the blood immediately penetrates through the layer and coagulates. Removal only induces minor post-operative or subsequent bleeding.

4 Summary

Observing the mean arterial blood pressure after the acute wound has been placed on the kidney and various materials have been applied indicates that FA 2(T) has a haemostatic effect which is comparable to that of the reference material and thereby reduces the drop-in blood pressure. From the even clearer reduction of the blood pressure drop with wound settlement after applying the dressing A I and especially A II and also the relatively low influence on haematocrit, a stronger blood coagulation promoting effect can be deduced from the wound dressings coated with halloy site. The small amount of blood and blood clots which collected in the abdominal cavity as well as the good capability to bind blood onto the material also prove the most effective blood coagulant promoting effect, particularly for A II.

What is claimed is:

1. A haemostatic wound dressing, wherein the haemostatic wound dressing has a textile substrate having a first surface and an opposing second surface, the textile substrate being a non-woven fabric, a woven material, a gauze, a knitted fabric, a crotched fabric, or a scrim; and
    comprises halloysite patterned layer only on portions of the first surface by silk screening;
    wherein the haemostatic wound dressing does not contain calcium-ion additives, wherein the halloysite is applied on the first surface of the textile substrate as a layer, the opposing surface being uncoated by additional halloysite content, wherein the textile substrate has a density between 30 g/m² and 120 g/m², and wherein the halloysite has been pretreated to convert Halloysite-10 Å to Halloysite-7 Å.

2. The haemostatic wound dressing according to claim 1, wherein the textile substrate further comprises composite fibres.

3. The haemostatic wound dressing according to claim 2, wherein the composite fibres comprise a mixture, and components of the mixture are selected from the group consisting of viscose, algae, milk protein fibres, and combinations thereof.

4. The haemostatic wound dressing according to claim 2, wherein the composite fibres are regenerated fibres.

5. The haemostatic wound dressing according to claim 1, wherein the halloysite is selected from the group consisting of Halloysite-7 Å, Halloysite-10 Å.

6. The haemostatic wound dressing according to claim 1, wherein the halloysite comprises halloysite nanotubes with the following dimensions: inner diameter: 10 to 20 nm (nanometre), external diameter: 50-70 nm, and length: 0.3-4 um (micrometre).

7. The haemostatic wound dressing according to claim 1, wherein the halloysite is applied to the textile substrate with a binding agent.

8. The haemostatic wound dressing according to claim 2, wherein the composite fibres comprise between 3% and 30% algae by volume, up to 100% milk protein by volume, or a combination thereof.

9. The haemostatic wound dressing according to claim 2, wherein additional halloysite at up to 30 volume % is incorporated into or onto the composite fibres themselves.

10. The haemostatic wound dressing according to claim 1, further comprising a binding agent that comprises 90%-95% by mass of deionized water and 5%-10% by mass of acrylate or gelatin.

11. The haemostatic wound dressing according to claim 1, wherein the halloysite covers at least 30% of a surface area of the first surface of the textile substrate.

12. The haemostatic wound dressing according to claim 1, wherein the haemostatic wound dressing comprises a halloysite content of 10 g/m²-60 g/m².

13. A method of treating an injured subject having a wound comprising: applying the haemostatic wound dressing according to claim 1 to the wound, and allowing sufficient time for the haemostatic wound dressing to treat the wound.

14. The method of claim 13 wherein the haemostatic wound dressing provides coagulation to the wound and does not cause new bleeding upon removal from the wound.

15. The method of claim 13 wherein the haemostatic wound dressing provides clot promotion to the wound.

16. The method of claim 13 wherein the haemostatic wound dressing provides biocidal effect to the wound.

17. The method of claim 13 wherein the wound is an acute wound.

* * * * *